United States Patent
Boonstra et al.

(10) Patent No.: US 6,232,430 B1
(45) Date of Patent: May 15, 2001

(54) CROSS-LINKERS FOR CROSS-LINKABLE OPTICAL POLYCARBONATES

(75) Inventors: Tjerk Oedse Boonstra, SK Duiven; Richard Herman Woudenberg, JG Elst; David van Olden, BJ Zevenaar, all of (NL)

(73) Assignee: JDS Uniphase Photonics C.V., Arnhem (NL)

( * ) Notice: Subject to any disclaimer, the term of this patent is extended or adjusted under 35 U.S.C. 154(b) by 0 days.

(21) Appl. No.: 09/284,886

(22) PCT Filed: Oct. 9, 1997

(86) PCT No.: PCT/EP97/05674

§ 371 Date: Aug. 4, 1999

§ 102(e) Date: Aug. 4, 1999

(87) PCT Pub. No.: WO98/17644

PCT Pub. Date: Apr. 30, 1998

(30) Foreign Application Priority Data

Oct. 23, 1996 (EP) .................................. 96202951

(51) Int. Cl.[7] .................................. C08G 64/00
(52) U.S. Cl. .................................. 528/196
(58) Field of Search .................................. 528/196, 198

(56) References Cited

FOREIGN PATENT DOCUMENTS

| | | |
|---|---|---|
| 2626832 | 12/1976 | (DE) . |
| 3443091 | 5/1986 | (DE) . |
| 3513715 | 10/1986 | (DE) . |
| 0645413 | 3/1995 | (EP) . |
| WO 96/28493 | 3/1996 | (WO) .................. C08G/64/15 |
| 9628757 | 9/1996 | (WO) . |

OTHER PUBLICATIONS

Endo, Masataka et al. "Pattern Formation of Resist With Deep UV Beam", Chemical Abstracts, vol. 111, No. 26 (Dec. 25, 1989).
Saida, Kenichi et al "Epoxy Resin Composites", Chemical Abstracts, vol. 92, No. 6 (Feb. 11, 1980).
Masayuki et al. "N–(Hydroxyphenyl)maleimides", Chemical Abstracts, vol. 91, No. 23 (Dec. 3,1979).
"Crosslinkable Aromatic Polyketones with Maleimide Pendent Groups" Mikroyannidis, Journal of Polymer Science, Part A: Polymer Chemistry vol. 28, pp. 669–677, 1990.

Primary Examiner—Terressa M. Boykin
(74) Attorney, Agent, or Firm—Dilworth & Barrese, LLP

(57) ABSTRACT

The invention pertains to a cross-linker of the formula

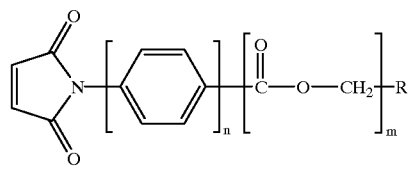

wherein
n is 0 or 1;
m is 0 or 1;
R is

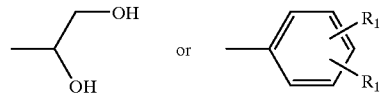

and $R_1$ is independently OH or —CO—O(hydroxyphenyl), or of the formula

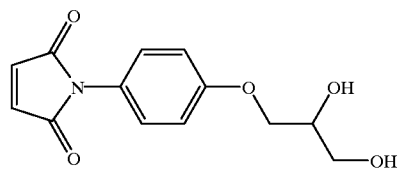

with the proviso that 3,4-dihydroxyphenylmaleimide is excluded. The invention further pertains to cross-linked optical polycarbonate and optical articles obtainable by cross-linking a polycarbonate with this cross-linker or with 3,4-dihydroxyphenylmaleimide.

16 Claims, No Drawings

CROSS-LINKERS FOR CROSS-LINKABLE OPTICAL POLYCARBONATES

BACKGROUND OF THE INVENTION

The present invention concerns cross-linkers for cross-linkable optical polycarbonates, cross-linked optical polycarbonates, and optical articles obtained therefrom.

In the field of optical polymers polycarbonates are preferred in view of their low light-absorbance in the wavelength area for optical uses (1270–1600 nm), making it possible to obtain optical components with low light loss. Polymeric optical components usually have a multilayer polymeric structure on a substrate with a guiding layer (the core layer) sandwiched between two polymer layers of a lower refractive index (cladding layers). Said layer structure can be formed conveniently by applying the various subsequent layers in the form of a solution, e.g. by means of spin-coating, followed by evaporation of the solvent. However, it was found that in layer-on-layer spin-coating the first polycarbonate layer re-dissolves on applying the next layer onto it. As it is essential for optical components to have a specific layer structure with each layer having a specific refractive index and layer thickness, such re-dissolving of the layers is a serious problem. Because no well-defined refractive index contrast and specific layer thickness can be obtained, the light traveling through the component is not confined within the core layer, resulting in substantial light losses. In EP-0,645,413 NLO (non-linear optical) polycarbonates are described. In order to solve the layer-on-layer spin-coating problem, it is suggested to introduce polyisocyanates or polyepoxides into the polycarbonate as a cross-linker. However, it proved quite hard to make a cross-linkable polycarbonate without detrimentally influencing the properties which determine the applicability of optical polycarbonates in optical components, such as Tg, refractive index, light loss, etc. For instance, it was found that the use of the polyisocyanate Desmodur N® posed problems due to swelling of the layers. Furthermore, it was found that even after curing the polycarbonate was still partly soluble in the spin-coating solvent. Also, the use of polyepoxides was not optimal. It was found that the layers could not be reproducibly obtained. Some of the layers were sound but others appeared to have cracks.

Earlier solutions to this problem were disclosed in our co-pending patent application PCT/EP96/01101, wherein a novel cross-linker has been disclosed. However, some applications demand considerable amounts of said cross-linker leading to cross-linked polycarbonates which are less suitable for optical application. Therefore a need exists for other cross-linkers having less disturbing optical properties. We have found that specific cross-linkers of the maleimide type can be applied to various types of polycarbonates, improving their properties considerably. Cross-linkers having a maleimide moiety as such are known, for example, the dichloro- and dimethyl-maleimide cross-linkers of German patent applications DE 3443091 and DE 3513715, and the 5-maleimido-isophthaloylchloride as disclosed by Mikroyannidis in J. Polymer Sci., Part A: Polymer Chemistry, 28 (1990), 669, and in German patent application DE 2626832. The use of these compounds for obtaining polycarbonates with advantageous optical properties is not disclosed in any of these prior art references.

In Chemical Abstracts, vol 111, no. 26 (abstract no. 244322) the compound 3,4-dihydroxyphenylmaleimide has been disclosed as an intermediate for the preparation of an amide derivative of maleic acid. No protection for this compound per se is sought.

The present invention provides novel cross-linkers for use in cross-linkable polycarbonates wherein the properties determining the applicability of the cross-linked polycarbonates in optical components are hardly detrimentally affected if at all, and the layers can be applied on top of each other without the first layer being re-dissolved. The novel cross-linkers make it superfluous to use tertiary amines as curing catalyst, which is of considerable advantage because tertiary amines degrade the polycarbonate. Small amounts of peroxide or even no catalyst at all suffice when using the novel cross-linkers. A further advantage is that polycarbonates having nitro groups can also be cross-linked, which is not possible with the known cross-linkers of the acrylate type. Another advantage of the presently claimed cross-linkers is the possibility to cure the polymer by irradiation with UV light, which introduces considerably less strain into the polymer than thermal curing. The novel cross-linkers provide cross-linked optical polycarbonates of excellent thermal stability.

SUMMARY OF THE INVENTION

The present invention therefore pertains in a cross-linker of the formula

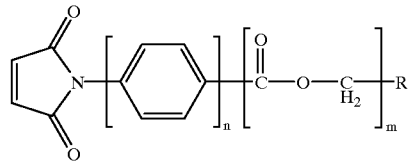

wherein n is 0 or 1;

m is 0 or 1;

R is

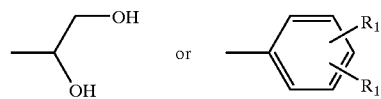

and $R_1$ is independently OH or —CO—O(hydroxyphenyl), with the proviso that 3,4-dihydroxyphenylmaleimide is excluded.

The term hydroxyphenyl means a phenyl group which is substituted with a hydroxy group at its ortho, meta, or para position. Preferably, the hydroxy group is attached to the para position of the phenyl group.

The $R_1$ groups can be attached to any position of the phenyl group. Preferably, the $R_1$ groups are bound to the two meta positions.

DESCRIPTION OF THE PREFERRED EMBODIMENTS

In order to obtain polycarbonates having properties optimized for particular applications, it is of particular interest to make mixtures of cross-linkers. It has been found that above-mentioned cross-linker in combination with

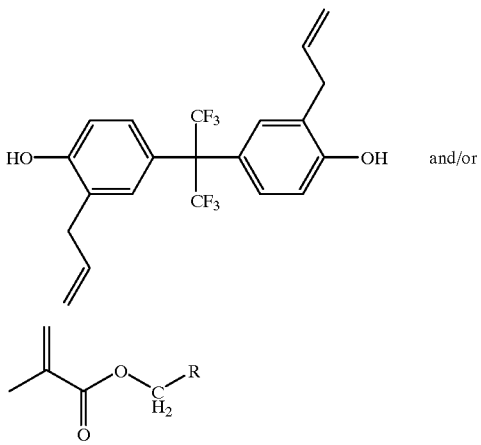

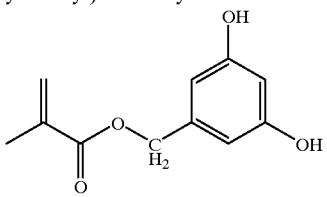

wherein R has the previously given meanings, afford a particularly useful cross-linking mixture for the manufacture of optical polycarbonates. Most preferred is the combination of the cross-linker of the invention with 3,5-dihydroxy-(phenylmethyl)methacrylate:

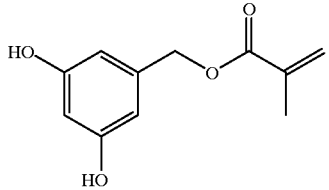

With the use of latter combination of cross-linkers, polymerization can take place separately from curing (cross-linking). The polymerization reaction of the polycarbonates can take place at approximately room temperature, while the curing reaction is performed either thermally (50 to 220° C., depending on the initiator used) or through photocuring with irradiation (UV or visible light). The optical polycarbonate obtained through cross-linking of a polycarbonate with the cross-linker according to the invention can be applied in a conventional way, for instance by spin-coating. After (or during) evaporation of the spin-coating solvent, the layer can be cured, so that the next layer can be applied without any problem. For thermal curing radical initiators, for instance, peroxides such as dicumyl peroxide, di-tert-butyl peroxide, dilauroyl peroxide, dibenzoyl peroxide, azobisisobutyronitrile (AIBN), and the like, can be included in the spin-coating solution. Suitable photo-initiators are for instance Irgacures® (Ciba Geigy) and Darocures® (Merck). The initiators are usually present in amounts ranging from 0.1 to 10% by weight calculated on the total weight of the polymer. The amount of cross-linker can vary between 5 and 50 mole % of the total monomer weight, but it is preferred to have more than 20 mole % of the cross-linker present in the monomer mixture. When more than 20 mole % of the cross-linker is used, layers of excellent quality, i.e. without cracks, can be obtained. The present invention is in the field of optical polycarbonates for use in optical components, in particular optical switches. The present invention provides a cross-linked optical polycarbonate built up from a polycarbonate and cross-linkers according to this invention.

The cross-linkers of the invention can be prepared by methods which are analogous to methods known for the preparation of related compounds. A suitable method is the condensation of maleic anhydride with an amine having the formula

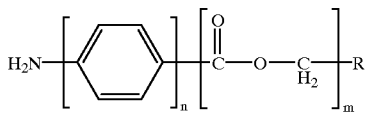

wherein $R_1$ n, and m have the previously given meanings, after which the maleic acid obtained can be ring closed to the maleimide cross-linker by converting the acid group of the maleic acid moiety into an activated group, for instance, an active ester of a halogenide, such as a chloride by reaction with. oxalyl chloride and triethylamine. The above-mentioned amines are known in the art, and preferably commercially available. Alternatively, an amine can be used, the side chain of which can be converted into a desired side chain by methods well known in the art and obvious for those skilled in the art. For instance, 4-(2-propenyloxy) phenylamine can be converted according to above-mentioned manner to 4-(2-propenyloxy)phenylmaleimide, after which the unsatured propenyl bond is oxidized with a peroxide such as m-chloroperbenzoic acid to an oxirane ring, which ring is ring opened by hydrolysis to the desired 4-(2,3-dihydroxypropyloxy)phenylmaleimide.

The invention further concerns the use of

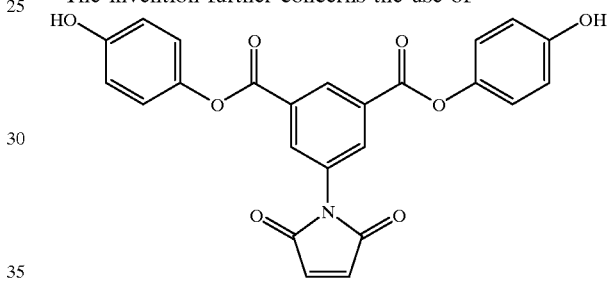

as a cross-linker for the preparation of optical polycarbonates and cross-linked optical polycarbonate obtainable by cross-linking a polycarbonate with the maleimide cross-linker of the invention, optionally, in combination with any of the other previously mentioned cross-linkers.

The invention also is concerned with an optical article, preferably, an optical switch comprising a polycarbonate cross-linked with the maleimide cross-linker of the invention, optionally, in combination with any of the other previously mentioned cross-linkers.

The invention is further illustrated by the following examples.

EXAMPLE 1

Resorcinol methacrylate (SKMA)

Methyl 3,5-di-tert-butyldimethylsilyloxybenzoate (step 1)

Methyl 3,5-dihydroxybenzoate (168 g, 1.00 mole) and tert-butyldimethylsilyl chloride (317 g, 2.10 mole) were dissolved in dry DMF (N,N-dimethyl formamide; 1000 ml). To the homogenous solution was added at once imidazole (145 g, 2.13 mole) and the reaction mixture was stirred overnight at room temperature (complete conversion TLC, dichloromethane:methanol 95:5). After the addition of water (1 1), the product was extracted into ether. The combined ether extracts were washed with water, brine, and dried over sodium sulfate. After the removal of the ether, p-xylene (500 ml) was added and evaporated (to remove the last traces of tert-butyldimethylsilyl chloride) under high vacuum (70° C. and 50 Pa) to obtain an oil.

3,5-Di-tert-butyldimethylsilyloxybenzyl alcohol (step 2)

Methyl 3,5-di-tert-butyldimethylsilyloxybenzoate (170 g, 0.429 mole) was dissolved in ether (800 ml) and cooled to 10° C. Lithium aluminum hydride (14.2 g, 0.374 mole) was added in small portions. After 0.5 h TLC revealed complete conversion (dichloromethane:methanol 95:5), and water (20 ml) was added dropwise to destroy the excess of lithium aluminum hydride. Water/formic acid 4:1 (500 ml) was added to dissolve the aluminum salts, the organic layer was separated, and the aqueous layer was extracted with ether. The combined ether layers were washed with 0.4M sodium hydroxide, water, and brine. After drying (sodium sulfate), the ether was removed in vacuo to yield 147 g of the benzyl alcohol (0.399 mole, 93%).

3,5-Di-tert-butyldimethylsilyloxybenzyl methacrylate (step 3)

3,5-Di-tert-butyldimethylsilyloxybenzyl alcohol (13.0 g, 35.2 mmole) and freshly distilled methacryloyl chloride (4.06 g, 38.8 mmole) were dissolved in 75 ml of ether and cooled to 0° C. Pyridine (3.21 g, 40.6 mmole) in ether (10 ml) was added dropwise and the reaction mixture was stirred overnight at room temperature. The pyridinium hydrochloride was filtered off and the filtrate was passed over a silica bed to remove the traces of methacrylic acid. Through the silica bed were passed another 75 ml of ether, and after combination of the fractions, the ether was removed under reduced pressure to obtain an oily product (14.2 g, 32.7 mmole, 93%).

3,5-Dihydroxybenzyl methacrylate (SKMA, step 4)

Concentrated hydrobromic acid (48%, 2.25 ml) was added dropwise to 3,5-di-tert-butyldimethylsilyloxybenzyl methacrylate (15.0 g, 34.4 mmole) and anhydrous potassium fluoride (7.5 g, 129 mmole) in acetonitrile (75 ml). After the solution was stirred overnight at room temperature, hydrochloric acid (4.5 ml conc. HCl in 30 ml of water) and 75 ml of dichloromethane were added to the pink solution. The organic layer was separated and the aqueous layer was extracted with dichloromethane. The organic layers were combined, washed with water and brine. The solution was dried twice over sodium sulfate, filtered over silica and after addition of toluene concentrated in vacuo. The oily residue was dissolved in isopropyl ether (38 ml) and precipitated in hexane (500 ml). The product was filtered off and recrystallized from isopropyl ether/hexane.

EXAMPLE 2

Dihydroxypropyl maleimide (DPMI)

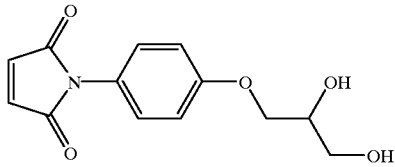

4-Allyioxyacetanilide (step 1)

4-Acetamidophenol (383 g, 2.53 mole), allyl bromide (338 g, 2.79 mole), and anhydrous potassium carbonate (350 g, 2.53 mole) were added to acetone (2250 ml). Under intense stirring, the heterogeneous mixture was refluxed overnight. After cooling, the inorganic salts were filtered off and the filtrate concentrated under reduced pressure. The obtained solid was used for step 2 without purification.

4-Allyloxyaniline (step 2)

4-Allylacetanilide (483 g, 2.53 mole) was added to a mixture of water (1100 ml) and concentrated hydrochloric acid (485 ml). The suspension was refluxed for 2 h, during which the 4-allylacetanilide dissolved (complete conversion on TLC dichloromethane:methanol 95:5). After cooling, sodium hydroxide (50%) was added dropwise until the solution was alkaline (PH>10) and the solution was extracted with ether. The ether extracts were combined, washed with 1M sodium hydroxide solution, water, and brine. After drying (sodium sulfate), the ether solution can be used as such in step 3.

4-Allyloxyphenylmaleamic acid (step 3)

The ether solution of 4-allyloxyaniline (step 2), or 4-allyloxyaniline (340 g, 2.28 mole) in 1.5 l ether was cooled to 15° C. Maleic anhydride (248 g, 2.53 mole) in dioxane (1200 ml) was added dropwise to the ether solution under cooling. After the addition, the suspension is stirred for 1 h at room temperature. The product was filtered off and washed with ether, and dried in a vacuum oven.

N-(4-allyloxyphenyl)chlorosuccinimide (step 4)

4-Allyloxyphenylmaleamic acid (247 g, 1 mole) and 11 drops of DMF were added to 1350 ml of dichloromethane. Oxalyl chloride (134 g, 1.05 mole) was added in 1 h, during which the temperature was kept at 10° C. After the addition, the temperature was raised to 15° C. for 0.5 h, followed by a further heating to 25° C. for 2 h. The clear brown solution was concentrated, and the solids were stripped with air. The crude product (266 g) was used without purification in step 5.

N-(4-Allyloxyphenyl)maleimide (step 5)

N-(4-Allyloxyphenyl)chlorosuccinimide (265.5 g, 1 mole) was dissolved in dichloromethane (1300 ml) and cooled to 10° C. Triethylamine (101 g, 1 mole) was added in 10 min and the reaction was stirred for 10 min. The reaction mixture was washed with 1M hydrochloric acid and dried over sodium sulfate. The organic solvent was removed under reduced pressure and the solid was recrystallized from methanol.

N-(4-[2,3-Epoxypropyl]oxyphenyl)maleimide (step 6)

N-(4-Allyloxyphenyl)maleimide (175 g, 76.4 mole) and 3-chloroperoxybenzoic acid (262 g, 70–75%, Across) were dissolved in 2.0 l of dichloromethane. After stirring for 72 h at room temperature, the reaction mixture was concentrated under reduced pressure to a slurry. Ether (2.0 l) was added to the slurry and stirred for 0.5 h at room temperature. The product was filtered off, washed with ether, and dried in an oven.

N-(4-[2,3-dihydroxypropyl]oxyphenyl)maleimide (=dihydroxypropylmaleimide [DPMI]) (step 7)

To a suspension of N-(4-[2,3-epoxypropyl]oxyphenyl) maleimide (200 g, 0.816 mole) in 1360 ml of acetone was added perchloric acid (20 ml) in 660 ml of water. The reaction mixture was refluxed for 2 h, during which the solution became clear yellow (complete conversion on TLC, dichloromethane: methanol 90:10). After cooling, the acetone was removed under reduced pressure. Water was added to the resulting slurry which was stirred for 0.5 h. The solids were filtered off, washed with water and dissolved in THF (tetrahydrofuran). This solution was dried twice over anhydrous sodium sulfate, followed by concentration to dryness.

The crude DPMI (100 g, 0.38 mole) was dissolved in acetonitrile (1000 ml) and filtered. The filtrate was concentrated to 330 g, followed by heating to dissolve the crystallized DPMI. After standing overnight, the crystals were filtered off and washed with toluene/acetonitrile (3:1). Concentration of the mother liquor afforded a second crop of crystals.

EXAMPLE 3
o,o'-Diallyl-F6-bisphenol-A (DABA)

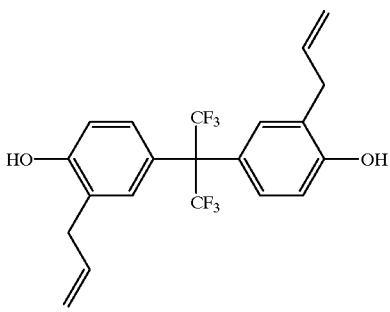

6-Bisphenol-A diallylether (step 1)

F6-Bisphenol-A (66.2 g, 0.20 mole), allyl bromide (58 g, 0.48 mole), and anhydrous potassium carbonate (66 g, 0.48 mole) were added to acetone (100 ml). Under intense stirring, the heterogeneous mixture was refluxed for 48 h (complete conversion on TLC). After cooling, water was added, and the aqueous mixture extracted with ether. The combined organic layers were washed with 1 M sodium hydroxide, water, and brine. After drying over sodium sulfate, the solvent was removed under vacuo, yielding 80.4 g (19.6 mole, 98%) of F6-bisphenol-A diallylether.

o,o'-Diallyl-F6-bisphenol-A (DABA)

F6-bisphenol-A diallylether (100 g, 0.243 mole) was heated to 235–240° C. under a nitrogen atmosphere. After cooling, the product was distilled under vacuo (250° C., 5 Pa), to yield 81 g (0.197 mole, 81%) of DABA.

EXAMPLE 4
N-[4-(2,3-dihydroxypropoxycarbonyl)phenyl]maleimide (DGly)

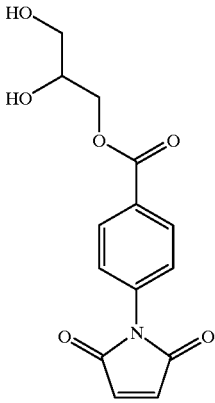

N-[4-(Chlorocarbonyl)phenyl]maleimide

N-[4-(Chlorocarbonyl)phenyl]maleimide was prepared according to the procedure described in J. Polym. Sci., Part A, Polymer Chem., Vol. 30, 1821–30 (1992).

N-[4-(2,2-dimethyl-1,3-dioxolane4-methoxycarbonyl )phenyi]maleimide. Solketal (25 g, 187 mmole) and triethylamine (21 g, 204 mmole) were dissolved in dichioromethane (200 ml) and added dropwise to N-[4-(chlorocarbonyl)phenyl]maleimide (40 g, 170 mmole) in dichloromethane (600 ml) at 0° C. After completion of the reaction (TLC), the reaction mixture was washed with water and brine. The solvent was evaporated in vacuo yielding 55 g (87%) of N-[4-(2,2-dimethyl-1,3-dioxclane-4-methoxy-carbonyl) phenyl]maleimide. This crude product was used in the deprotection step.

N-[4-(2,3-dihydroxypropoxycarbonyl)phenyl]maleimide

N-[4-(2,2-dimethyl-1,3-dioxolane4-methoxycarbonyl) phenyl]maleimide (40 g, 120 mmole) was dissolved in 300 ml of THF and 100 ml 25% of acetic acid solution. The reaction mixture was refluxed for 10 min and then cooled to room temperature. The solvents were evaporated under reduced pressure and 25.5 g of the residue was purified using column chromatography over silica with hexanelethyl acetate (1:4) as eluent. Yield of pure diol 10.47 g.

EXAMPLE 5
N-[3, 5-di(4-hydroxyphenoxycarbonyl)phenyl]maleimide (DHPM)

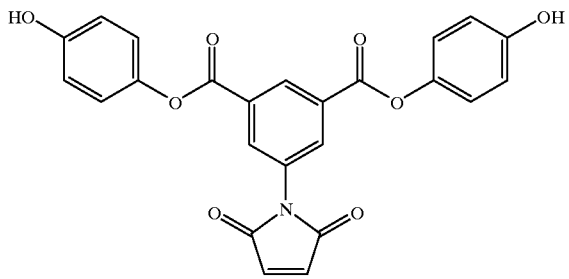

1 -(Benzyloxy)-4-(tert-butyldimethylsilyloxy)benzene

4-Benzyloxyphenol (39 g, 0.19 mole) and tert-butyldimethylsilyl chloride (32.31 g, 0.21 mole) were dissolved in dimethylformamide (200 ml). Imidazole (14.59 g, 0.21 mole) was added in portions and after the addition the reaction mixture was stirred overnight. Water was added and the mixture was extracted with ether. The combined organic layers were washed with water and dried over anhydrous calcium chloride. The solvent was evaporated to yield crystallized product (60.2 g, 0.19 mole, 98%).

4-(tert-Butyldimethylsilyloxy)phenol 1-(Benzyloxy)-4-(tert-butyldimethylsilyloxy)benzene was dissolved in ethyl acetate (400 ml) and 5 g of palladium on active carbon (5%) were added. After hydrogenation, the catalyst was removed by filtration and the solvents were removed under vacuo, to yield 42 g of 4-(tert-butyldimethylsilyloxy)-phenol (97%).

N-[3,5-di-(4-(tert-Butyldimethylsilyloxy)phenoxycarbonyl) phenyl]maleimide

5-Maleimido-isophthaloyl chloride (prepared according to the procedure described in DE 2626832) (33 g, 0.11 mole) and 4-(tert-butyldimethyl-silyloxy)phenol (49.55 g, 0.22 mole) were dissolved in THF (600 ml) and cooled to 0° C. Triethylamine (22.9 g, 0.23 mole) in THF (80 ml) was added dropwise. The reaction mixture was warmed to room temperature and after 0.5 h, the triethylamine hydrochloride was filtered off. The solvents were removed under reduced pressure and the product was purified by column chromatography over silica. Yield of product (36 g, 0.07 mole, 60%).

N-[3,5-di-(4-hydroxyphenoxycarbonyl)phenyl]maleimide

N-[3,5-di-(4-(tert-butyldimethylsilyloxy) phenoxycarbonyl)phenyl]maleimide (35 g 0.052 mole) was dissolved in THF (500 ml). Hydrogen fluoride (2.5 M, 70 ml), sodium fluoride (3 g) and water (280 ml) were added. The reaction mixture was stirred overnight and most of the solvent was removed. Filtration of the product over a silica bed and concentration in vacuo afforded N-[3,5-di-(4-hydroxyphenoxycarbonyl)phenyl]maleimide (22.2 g, 96%).

EXAMPLE 6

General polymerization procedure

To a well stirred mixture of 50 mole % of a carbonate monomer (e.g. hexafluoro-bisphenol-bischloroformate; tetrabromo-hexafluorobisphenol-bischloroformate) and 50 mole % of a diol (e.g. hexafluoro-bisphenol-A; tetrabromo-hexafluorobisphenol-A; bis-(p-hydroxyphenyl)-bisphenyl methane; 2,2,3,3,4,4,5,5-octafluoro-1.6-dihydroxyhexane) are added in a suitable solvent (e.g., THF; THF/dichloromethane 1/4 v/v). The diols comprise one or more cross-linkers according to this invention, and optionally other diols. A pyridine solution in THF was added dropwise, while the temperature was kept at 0–10° C. After 4 h the reaction product was precipitated in alcohol (methanol).

Tg's for the SKMA/DPMI and F8 containing polycarbonates before and after curing:

F6BA=hexafluorobisphenol-A

F6Br4BA=hexafluoro-2,2',6,6'-tetrabromobisphenol-A

P4-diol=4,4'-dihydroxytetraphenylmethane

F8-diol=2,2,3,3,4,4,5;5-octafluorohexane-1,6-diol

MGly=N-[2,3-dihydroxypropoxycarbonyl)phenyl] maleimide

DHPM=N-[3,5-di(4-hydroxyphenoxycarbonyl)phenyl] maleimide

DABA=o,o'-diallyl-hexafluoro-bisphenol-A

| Polymer composition (mole %) | | | | | before curing | | | after curing |
|---|---|---|---|---|---|---|---|---|
| F6BA | DPMI | SKMA | P4-diol | F8-diol | MW (× 10³) | Tg | Initiator[a] (%) | Tg[b] |
| 81 | 5 | 14 | 0 | 0 | 21 | 130/137 | 0 | 153/170 |
| 81 | 5 | 14 | 0 | 0 | 21 | 130/137 | 5 | 172/189 |
| 81 | 7 | 12 | 0 | 0 | 47 | 138/143 | 0 | 147/168 |
| 81 | 7 | 12 | 0 | 0 | 47 | 138/143 | 5 | 186/199 |
| 66 | 5 | 14 | 15 | 0 | 30 | 140/146 | 2 | 182/197 |
| 66 | 5 | 14 | 15 | 0 | 30 | 140/146 | 5 | 185/200 |
| 61 | 5 | 14 | 20 | 0 | 10 | 134/139 | | |
| 56 | 5 | 14 | 25 | 0 | 10 | 134/141 | 2 | 162/179 |
| 56 | 5 | 14 | 25 | 0 | 9 | 137/141 | 5 | 170/186 |
| 56 | 5 | 14 | 0 | 25 | 174 | 99/105 | 5 | 112/146 |
| 50 | 5 | 14 | 16 | 15 | 115 | 125/130 | 2 | 140/169 |

[a]The initiator is dicumyl peroxide
[b]Tg taken from third heating curve (DSC, 20° C./min)

EXAMPLE 7

Tg's for the DPMI/DABA containing polycarbonates before and after curing:

| Polymer composition (mole %) | | | | | before curing | | | after curing |
|---|---|---|---|---|---|---|---|---|
| F6BA | DPMI | DABA | P4-diol | F8-diol | MW (× 10³) | Tg | Initiator[a] (%) | Tg[b] |
| 77.5 | 17.5 | 5.0 | 0 | 0 | 16 | 128/133 | | 153/173 |
| 77.1 | 18.7 | 4.2 | 0 | 0 | 17 | 129/135 | 0 | 141/151 |
| 77.1 | 18.7 | 4.2 | 0 | 0 | 17 | 129/135 | 5 | 195/205 |
| 77.1 | 18.7 | 4.2 | 0 | 0 | 17 | 129/135 | 2 | 185/204 |
| 79.6 | 14.2 | 6.2 | 0 | 0 | 21 | 136/140 | 2 | 179/192 |
| 87.9 | 8.5 | 3.6 | 0 | 0 | 21 | 143/148 | | |
| 50.1 | 19.8 | 8.6 | 21.5 | 0 | 29 | 136/143 | 0 | 145/154 |
| 50.1 | 19.8 | 8.6 | 21.5 | 0 | 29 | 136/143 | 2 | 203/214 |
| 56.6 | 19.8 | 8.6 | 15.0 | 0 | 25 | 136/142 | | |
| 61.5 | 19.8 | 8.6 | 10.1 | 0 | 25 | 134/140 | | |
| 58.6 | 19.8 | 8.6 | 0 | 12.8 | 31 | 112/117 | 0 | 119/132 |
| 58.6 | 19.8 | 8.6 | 0 | 12.8 | 31 | 112/117 | 2 | 163/200 |
| 50.1 | 19.8 | 8.6 | 0 | 21.5 | 35 | 98/104 | 2 | 135/177 |
| 50.0 | 14.0 | 6.0 | 0 | 30.0 | 55 | 90/95 | 2 | 98/118 |
| 50.0 | 14.5 | 6.5 | 14.5 | 14.5 | 33 | 120/127 | 2 | 159/183 |

[a]The initiator is dicumyl peroxide
[b]Tg taken from third heating curve (DSC, 20° C./min)

EXAMPLE 8

Tg's for the DGly/DHPA containing polycarbonates before and after curing:

| Polymer composition (mole %) | | | | MW | |
|---|---|---|---|---|---|
| F6BA | DGly | DHPM | F6Br4BA | (× 10³) | Tg |
| 75 | 25 | 0 | 0 | 59 | — |
| 75 | 0 | 25 | 0 | 11 | 163/169 |
| 85 | 0 | 15 | 0 | 16 | 161/169 |
| 90 | 0 | 10 | 0 | 21 | 163/171 |
| 50.0 | 0 | 25 | 25 | 16 | — |

What is claimed is:

1. A cross-linker of the formula

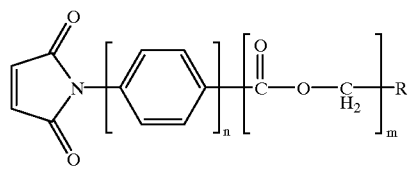

wherein n is 0 or 1;

m is 0 or 1;

R is

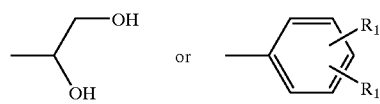

and $R_1$ is independently OH or —CO—O (hydroxyphenyl), or of the formula

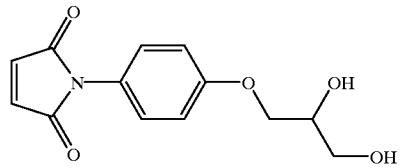

with the proviso that 3,4-dihydroxyphenylmaleimide is excluded.

2. The cross-linker of claim 1 in combination with

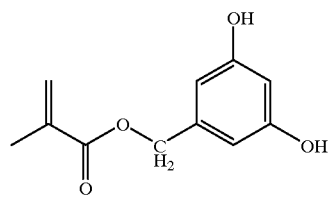

3. The reaction product of the cross-linker of claim 1 with at least one of the compounds selected from the group consisting of

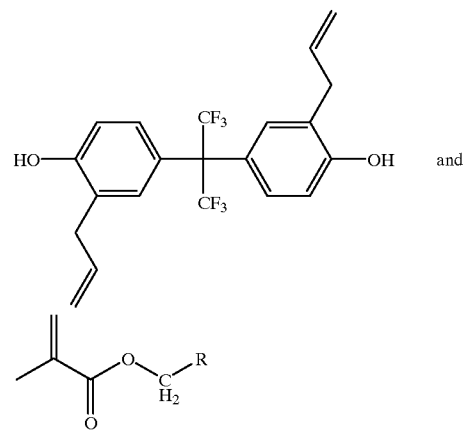

wherein R is

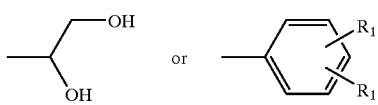

and $R_1$ is independently OH or —CO—O (hydroxyphenyl).

4. A cross-linker consisting of the reaction product of 3,4-dihydroxyphenylmaleimide with at least one of the compounds selected from the group consisting of

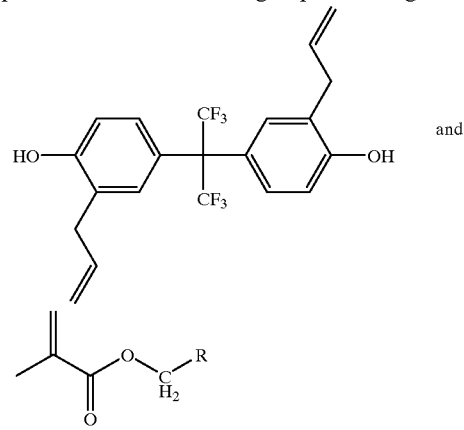

wherein R is

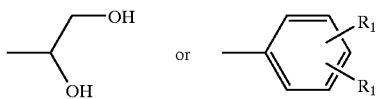

and $R_1$ is independently OH or —CO—O (hydroxyphenyl).

5. A cross-linker consisting of the reaction product of 3,4-dihydroxyphenylmaleimide with

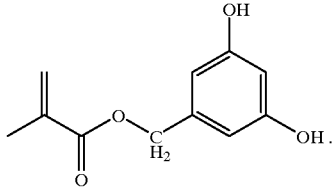

6. A cross-linker for the preparation of optical polycarbonates having the following structural formula

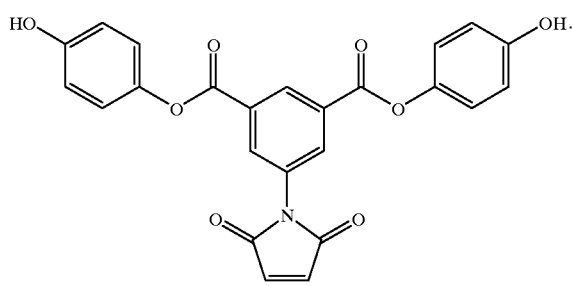

7. A cross-linked optical polycarbonate prepared by the process of cross-linking a polycarbonate with the cross-linker of claim 1.

8. A cross-linked optical polycarbonate prepared by the process of cross-linking a polycarbonate with at least one cross-linker selected from the group consisting of the cross-linker of claim 2 and

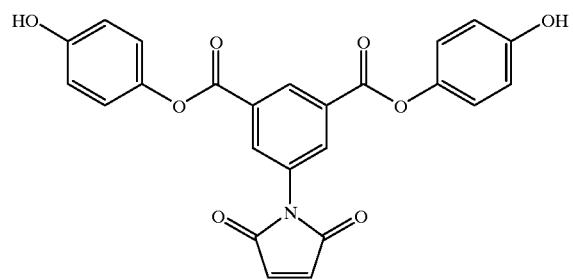

or the reaction product thereof.

9. A cross-linked optical polycarbonate prepared by the process of cross-linking a polycarbonate with at least one cross-linker selected from the group consisting of the cross-linker of claim 3 and

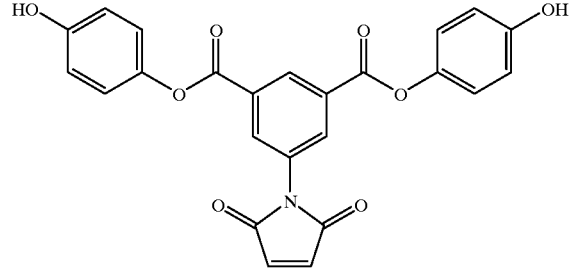

or the reaction product thereof.

10. A cross-linked optical polycarbonate prepared by the process of cross-linking a polycarbonate with at least one cross-linker selected from the group consisting of the cross-linker of claim 4 and

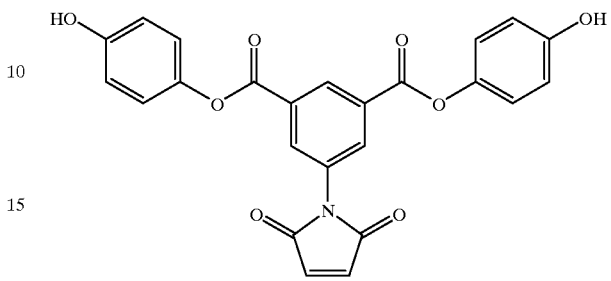

or the reaction product thereof.

11. A cross-linked optical polycarbonate prepared by the process of cross-linking a polycarbonate with at least one cross-linker selected from the group consisting of the cross-linker of claim 5 and

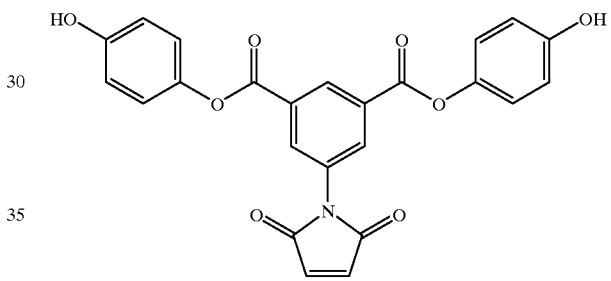

or the reaction product thereof.

12. An optical article comprising the cross-linked optical polycarbonate of claim 7.

13. An optical article comprising the cross-linked optical polycarbonate of claim 8.

14. An optical article comprising the cross-linked optical polycarbonate of claim 9.

15. An optical article comprising the cross-linked optical polycarbonate of claim 14.

16. An optical article comprising the cross-linked optical polycarbonate of claim 11.

* * * * *